United States Patent [19]
Gedeon

[11] Patent Number: 5,468,451
[45] Date of Patent: Nov. 21, 1995

[54] DEVICE FOR INDICATING THE PRESENCE OF CARBON DIOXIDE IN A PATIENT'S EXHALED AIR

[75] Inventor: Andras Gedeon, Täby, Sweden

[73] Assignee: Minco AB, Täby, Sweden

[21] Appl. No.: 190,189

[22] PCT Filed: Jun. 22, 1993

[86] PCT No.: PCT/SE93/00554

§ 371 Date: Feb. 10, 1994

§ 102(e) Date: Feb. 10, 1994

[87] PCT Pub. No.: WO94/00756

PCT Pub. Date: Jan. 6, 1994

[30] Foreign Application Priority Data

Jun. 29, 1992 [SE] Sweden ................................ 9201995

[51] Int. Cl.$^6$ ................................................. A61B 5/097
[52] U.S. Cl. .............................. 422/58; 422/85; 128/719
[58] Field of Search ............................... 422/55, 56, 57, 422/58, 59, 85, 86, 87; 436/68, 133, 163, 165, 169; 128/719, 207.14

[56] References Cited

U.S. PATENT DOCUMENTS

| | | |
|---|---|---|
| 2,136,236 | 11/1938 | Draper . |
| 2,890,177 | 6/1959 | Kilmer . |
| 3,373,735 | 3/1968 | Gallager . |
| 3,507,623 | 4/1970 | McConnaughey . |
| 4,558,708 | 12/1985 | Labuda et al. . |
| 4,691,701 | 9/1987 | Williams . |
| 4,728,499 | 3/1988 | Fehder . |
| 4,790,327 | 12/1988 | Despotis . |
| 4,879,999 | 11/1989 | Leiman et al. . |
| 5,124,129 | 6/1992 | Riccitelli et al. ..................... 422/56 |

FOREIGN PATENT DOCUMENTS

| | | |
|---|---|---|
| 750997 | 10/1951 | Germany . |
| 919510 | 10/1954 | Germany . |
| 1006183 | 4/1957 | Germany . |
| 1007525 | 5/1957 | Germany . |
| 1029525 | 5/1958 | Germany . |
| 1037725 | 8/1958 | Germany . |
| 1145387 | 3/1963 | Germany . |
| 2218515 | 11/1989 | United Kingdom . |

OTHER PUBLICATIONS

Adriani, *Carbon Dioxide Absorption*, The Chemistry and Physics of Anesthesia, Chapter 5, Second Edition, pp. 151, 176–177, 179–183, 1962.

Adriani, *Disposal of Carbon Dioxide from Devices used for Inhalational Anesthesia*, Anesthesiology, vol. 21, no. 6, pp. 742–758, Nov.–Dec. 1960.

Berman, *the Einstein Carbon Dioxide Detector*, Anesthesiology, vol. 60, No. 6, pp. 613–614, Jun. 1984.

(List continued on next page.)

Primary Examiner—Jeffrey R. Snay
Attorney, Agent, or Firm—Browdy and Neimark

[57] ABSTRACT

A device for indicating the presence of $CO_2$ in a patient's inhaled air comprises a $CO_2$ detector including an indicator element (14) which undergoes a reversible color change in response to exposure thereof to air containing $CO_2$ in concentrations of the same order of magnitude as the $CO_2$ concentration of air exhaled by a human being, and also comprises a heat-moisture exchanger (12) including a housing (13) with a first connecting port (15) adapted to be connected to the trachea of a patient, and a second connecting port (15) adapted for connection to a ventilator or an anesthetic machine, for example. In a flow-through passage (P) extending between the connecting ports (15, 16) there is mounted an element (18) for the regenerative exchange of heat and moisture between, on the one hand, air flowing through the flow-through passage (P) in one direction and, on the other hand, air flowing through the flow-through passage (P) in the opposite direction. The indicator element (14) is disposed in the flow-through passage on the side of the heat-moisture exchanger element (18) remote from the first connecting port (15) and is viewable from outside the housing, and its response time for the color change is sufficiently short to enable it to change color upon each breath.

4 Claims, 1 Drawing Sheet

OTHER PUBLICATIONS

Guedel et al., *A New Intratracheal Catheter*, Anesthesia and Analgesia, vol. 7, pp. 238–239, Jul.–Aug. 1928.

Draper et al, *A Proposed Device which is Capable of Continuously Indicating the Approximate Percentage of Carbon Dioxide in a Stream of Flowing Gases*, Colorado Medicine, vol. 32, pp. 899–900, Nov. 1935.

Smith et al, *Simple Method of Determining $CO_2$ Content of Alveolar Air*, Anesthesiology, vol. 20, no. 5, pp. 702–703, Sep.–Oct. 1959.

Smith, *Design and Function of Pediatric Anesthesia Systems*, Anesthesia for Infants and Children, Chapter 6, Fourth Edition, pp. 128–130, 1980.

Waters, *Advantages and Technique of Carbon Dioxid Filtration with Inhalation Anesthesia*, Anesthesia and Analgesia, vol. 5, pp. 160–162, Jun. 1926.

DEVICE FOR INDICATING THE PRESENCE OF CARBON DIOXIDE IN A PATIENT'S EXHALED AIR

FIELD OF THE INVENTION

This invention relates to a device for indicating the presence of carbon dioxide, $CO_2$, in the air exhaled by a patient. More particularly, the invention relates to a device of the kind comprising an indicator element which undergoes a reversible change of colour in response to the exposure thereof to air containing $CO_2$ in concentrations of the same order of magnitude as the $CO_2$ concentration of air exhaled by a human being.

DESCRIPTION OF THE RELATED ART

Indicator elements of this kind are known per se, see, for example, U.S. Pat. No. 4,728,499, WO89/07957 and WO91/05252. A major use of such indicator elements is to indicate the proper intubation of a patient's trachea (windpipe). This use relies on the fact that air exhaled by a human being contains $CO_2$ in much higher concentrations, 4 to 6 percent, than does the air in the oesophagus (gullet), the $CO_2$ concentration of which is approximately equal to that of the atmospheric air and thus is only a few hundredths of one percent.

Thus, with proper intubation, the air exhaled through the intubation tube, such as a tracheal catheter, will have a relatively high concentration of $CO_2$ and will, therefore, cause a colour change of an indicator element of the above-mentioned kind which is located in the exhalation path, e.g. at the distal end of the intubation tube. For obvious reasons, the indicator element should be located such that it is readily viewable from the outside, and if its response is sufficiently rapid, it will change colour immediately upon the first exhalation and, consequently, will immediately indicate that the intubation tube does in fact extend into the trachea as desired, and not into the oesophagus.

If the indicator element responds sufficiently rapidly, the colour change will reverse on each inhalation and occur again on each exhalation. Known in the art are indicator elements which respond sufficiently rapidly to be able to follow the changes of the $CO_2$ concentration with inhalations and exhalations at the normal respiration rate, which is on the order of 10 breaths per minute.

It has been found, however, that the response time increases gradually with the number of exhalations so that the indicator element will be unable to follow the changes after a number of exhalations have taken place. This increase of the response time causes no problem in the above-described use in which it is sufficient to detect that the intubation was successful, because, in principle, a single colour change suffices for that purpose. However, in cases in which it is desired to monitor the breathing in respect of the presence of $CO_2$ for a longer period, such as for an hour or a few hours, known indicator elements are not suitable. In such cases, therefore, it has been necessary to rely on other types of $CO_2$ detecting devices, primarily electrical instruments.

The reason why the response time of the known indicator elements increases gradually may be that the balance of the amount of water bound to the indicator element against the desired response time is upset under the influence of the moisture contained in the exhaled air.

An object of the invention is to provide an indicating device of the kind mentioned above which is capable of indicating the presence of $CO_2$ in a patient's exhaled air over an extended period of time, namely such that a colour change of the $CO_2$ indicator element is brought about and reversed with each breath of the patient throughout the monitored period.

This object is achieved with the construction of the indicating device which is set forth below.

SUMMARY OF THE INVENTION

The construction of the indicating device according to the invention is based on the concept of providing for the $CO_2$ to operate in an environment which is of a character such that the amount of water in the indicator element, which amount has been selected or determined in connection with the preparation of the indicator element during its manufacture, remains substantially unchanged for a substantial period of time, such as 1 to 5 hours.

According to the invention, the indicator element is incorporated in a regenerative heat-moisture exchanger, namely at the section of the flow-through air passage thereof which in use is remote from the respiratory tract of the patient and separated from the respiratory tract by the moist-absorbing element of the heat-moisture exchanger.

The heat-moisture exchanger may be of a type which is known per se; several of the commercially available single-use heat-moisture exchangers can quite easily be modified and equipped with a $CO_2$ indicator element of the kind contemplated here. Naturally, its housing, or at least the part of the housing where the indicator element is located, should be transparent so that the indicator element can readily be viewed by a person who monitors the breathing of the patient.

BRIEF DESCRIPTION OF THE DRAWING FIGURES

The invention is illustrated in the accompanying drawing which shows an exemplary embodiment.

DETAILED DESCRIPTION OF THE PREFERRED EMBODIMENT

Figure 1:
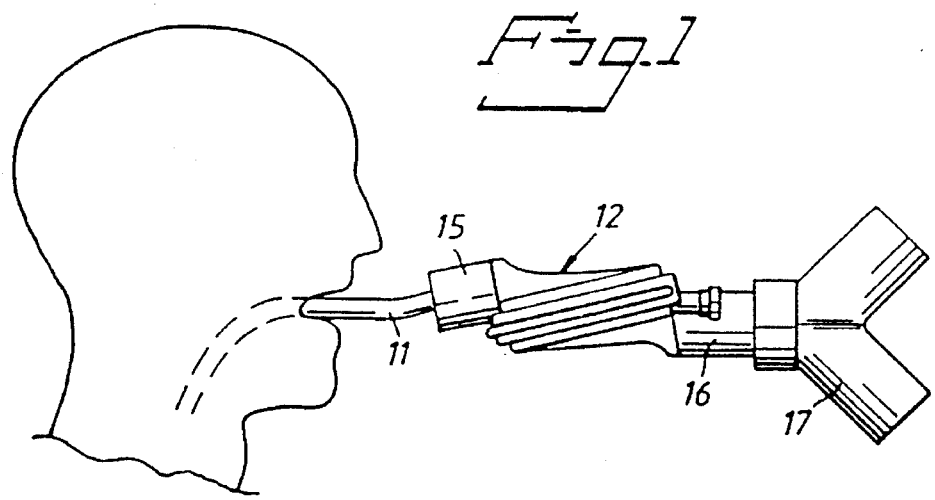
FIG. 1 is a diagrammatic view which shows the use of the device according to the invention.
Figure 2:
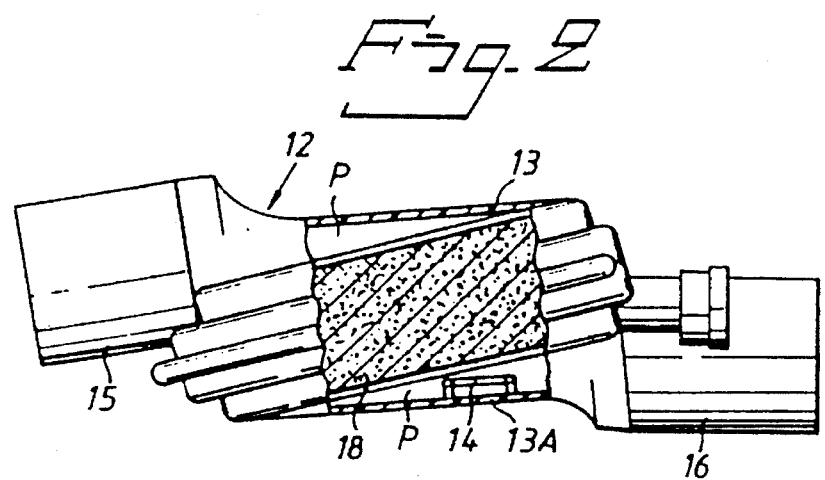
FIG. 2 is a side view of the device in FIG. 1, certain portions being shown in section.
Figure 3:
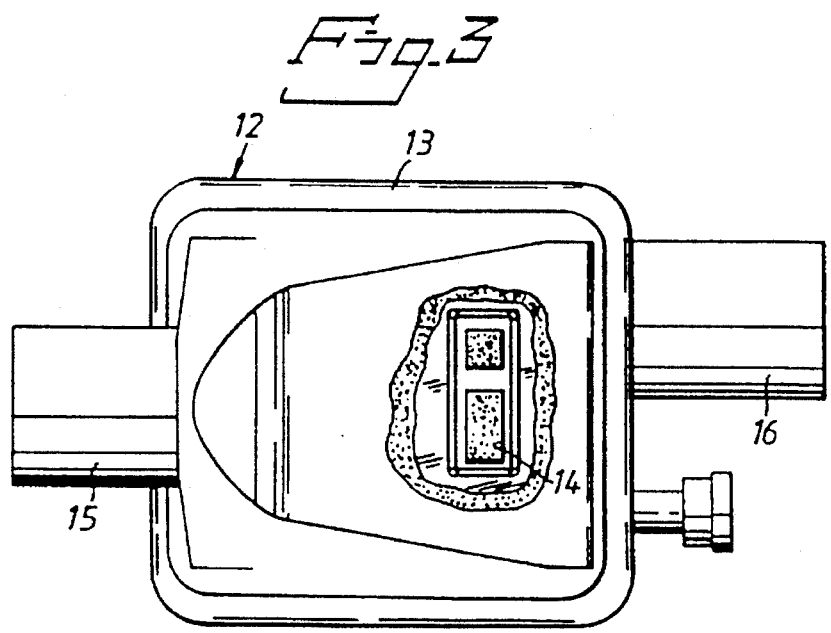
FIG. 3 is a plan view of the device shown in FIG. 2 with certain portions of the housing of the device and the heat-moisture exchanger mounted inside the housing being broken away so that the indicator element can be seen.

FIG. 1 shows a patient with an inserted tracheal catheter 11 the distal end of which is connected to a regenerative heat-moisture exchanger 12, inside the housing 13 of which a $CO_2$ indicator element 14 of the kind mentioned above is mounted. The patient may be connected to a ventilator or an anaesthetic machine, which, however, is not shown in the drawing.

Apart from the indicator element 14, the heat-moisture exchanger 12 may be of any known design. One side of the exchanger housing 13 is provided with a connecting port 15, hereinafter referred to as the wet connector, which is connected to the tracheal catheter 11. On the opposite side, the housing 13 has a similar connecting port 16, hereinafter referred to as the dry connector, by which the housing is connected to the ventilator or anaesthetic machine through the intermediary of a conventional Y-piece 17. On the side of the housing 13 where the dry connector 16 is provided, the housing has a further port which is used for measuring or monitoring purposes.

The open space in the housing between the connectors 15 and 16 defines a flow-through passage P through which the air flows between the connectors when the patient breathes. The main portion of the flow-through passage is occupied by a heat-moisture exchanger element (hygroscopic condenser/humidifier) 18 of a kind well known per se, which is arranged such that the air is forced to flow through it when the patient breathes. Upon exhalation, the heat-moisture exchanger element 18 absorbs moisture from the exhaled air and thereby absorbs a large portion of the heat content of the air. Upon inhalation, the inhaled air is humidified and heated in the exchanger element because it absorbs moisture and heat which has been given up to the exchanger element during the exhalation.

In the illustrated example, the indicator element 14 is a rectangular sheet which is mounted in the housing 13 such that when the patient breathes, both when he inhales and when he exhales, the indicator element is contacted on both sides by the air at the side of the heat-moisture element 18 which is closest to the dry connector 16.

Because the exhaled air is relatively dry when it contacts the indicator element 14 after having given up most of its moisture content Go the heat-moisture exchanger element 18 and because the inhaled air is also relatively dry before it enters the heat-moisture exchanger element, the indicator element 14 constantly operates in an environment of low and substantially constant moisture content. For that reason, the indicator element can operate for a comparatively long time without the moisture balance in it becoming substantially upset. It therefore is capable of responding rapidly to $CO_2$ concentrations above the value for which it has been set, and it is thus capable of undergoing a colour change upon each breath over a long period of time.

The indicator element 14 can be designed and arranged in many different ways within the scope of the invention. Naturally, it should be arranged such that it is effectively contacted by the flowing air during both the inhalation and the exhalation. Obviously, it is important that it can be viewed from outside the housing 13 so that the colour changes can be observed visually. The housing should therefore be transparent at least at the side where the indicator element is located; suitably, the entire housing 13 or the housing portion 13A located opposite to the indicator element 14 consists of clear transparent plastic.

Preferably, the indicator element 14 is adapted to the temperature and relative humidity of the environment in which it is expected to operate inside the heat-moisture exchanger during use of the indicating device, more particularly during exhalation.

In a preferred embodiment, the indicator element is therefore prepared during the manufacture thereof in a manner such that it operates optimally in the conditions which may be expected to exist at the dry connector 16 during the exhalation. Following such preparation, the indicator element is sealed in the heat-moisture exchanger in such a manner, e.g. by enclosing the entire heat-moisture exchanger with the indicator element inserted therein in a moisture-tight envelope, that it is not affected by varying humidity of the environment until the seal is broken, normally immediately prior to the actual use.

In one embodiment, the indicator element is therefore optimised for a certain range of relative humidity and a certain temperature range. Generally, optimisation for the range of 20–45% relative humidity and a temperature range of 21°–24° C. is suitable and preferable. Optimisation for the upper regions of these ranges characterises an embodiment intended primarily for use during anaesthesia, while an Optimisation for the lower regions of the ranges characterises an embodiment which is intended primarily for use in intensive care.

I claim:

1. A device for indicating presence of $CO_2$ in a patient's exhaled breath, comprising:

a $CO_2$ detector including an indicator element which undergoes a reversible color change in response to exposure thereof to air containing $CO_2$ in concentrations of a same order of magnitude as a $CO_2$ concentration of the patient's exhaled breath;

a heat-moisture exchanger further comprising a housing which includes a first connecting port adapted to be connected to the trachea of a patient and a second connecting port adapted to be connected selectively to a ventilator and an anaesthesia machine and which has mounted in a flow-through passage extending between the connecting ports an exchanger element for the regenerative exchange of heat and moisture between firstly, air which flows through the flow through passage in one direction and, secondly, air which flows through the flow-through passage in an opposite direction;

the indicator element being disposed in the flow-through passage away from and on the downstream side of the heat-moisture exchanger element in direction of flow of the patient's breath and remote from the first connection port, said indicator element being viewable from outside the housing;

the indicator element having a response time for colour changes responsive to $CO_2$ which is sufficiently short to enable the indicator element to change color upon each breath.

2. The device according to claim 1, wherein the indicator element is viewable through a transparent section of a wall of the housing.

3. A device for endotracheal intubation of a patient, having a color-reversible colorimetric indication of $CO_2$ in exhaled air, comprising:

a housing having a first port connectable with the patient's trachea, a second port connectable with a medical ventilating apparatus, and a flow-through passage therebetween;

a heat/moisture exchanger element disposed across the flow-through passage in a substantially gas-sealing manner, whereby gas moving between the first port and the second port passes through the exchanger element;

a $CO_2$ indicator element which changes color upon contact with $CO_2$, said indicator element being disposed at least partially within the passage between the exchanger element and the second port so that said indicator element is in contact with gas flowing through said passage, the indicator element being viewable from outside of the housing;

the indicator element having a color response time such that an indicating color thereof changes in an average breath cycle of inhalation and exhalation.

4. The device according to claim 3, wherein the indicator element is disposed within the housing and the housing is transparent.

* * * * *